(12) United States Patent
Persson

(10) Patent No.: US 6,261,098 B1
(45) Date of Patent: Jul. 17, 2001

(54) ARRANGEMENT FOR RECREATING A MODEL OF A DENTAL PRODUCT

(75) Inventor: Magnus Persson, Vänersborg (SE)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/381,311

(22) PCT Filed: Mar. 19, 1998

(86) PCT No.: PCT/SE98/00492

§ 371 Date: Oct. 22, 1999

§ 102(e) Date: Oct. 22, 1999

(87) PCT Pub. No.: WO98/44864

PCT Pub. Date: Oct. 15, 1998

(30) Foreign Application Priority Data

Apr. 10, 1997 (SE) .................................... 9701308

(51) Int. Cl.[7] .................................................. A61C 13/00
(52) U.S. Cl. .......................................... 433/213; 433/223
(58) Field of Search .................................. 433/213, 172, 433/223; 700/163, 160

(56) References Cited

U.S. PATENT DOCUMENTS

| | | | |
|---|---|---|---|
| 5,452,219 | * 9/1995 | Dehoff et al. | 433/223 |
| 5,779,477 | 7/1998 | Boss . | |
| 5,816,810 | 10/1998 | Antonson et al. . | |
| 5,851,115 | * 12/1998 | Carlsson et al. | 433/223 |
| 5,857,853 | * 1/1999 | Van Nifterick et al. | 433/213 |
| 5,938,446 | 8/1999 | Andersson et al. . | |

\* cited by examiner

Primary Examiner—Todd E. Manahan
(74) Attorney, Agent, or Firm—Connolly Bove Lodge & Hutz

(57) ABSTRACT

In an arrangement for recreating a model, use is made of an original model (1) of implant and/or tooth remnants (2–5) in a system for producing a dental construction (32). The system includes a reading apparatus (10, 13) and a first levelling function (6). A reproduction of all or part of the original model is created in CAD equipment. The said dental construction is created in the CAD equipment, and the reproduction and the construction are divided up into parts whose axes of inclination and contact surfaces are identified in terms of position and direction. Replicas of the implant and/or tooth remnant parts and the construction parts are produced and mounted on a mounting member (23) after bore holes for the replicas of the tooth remnant parts have been established using boring equipment. The said bore holes are established by means of a second levelling function and the bore holes receive positions and longitudinal axis inclinations which correspond to the positions and the inclinations of corresponding axes in the original model. The replicas for the tooth remnant parts can be fixed in terms of angle of rotation in the mounting member with position-fixing members (identification members). The last-mentioned replicas form the recreated model on which the construction replicas can be applied.

9 Claims, 3 Drawing Sheets

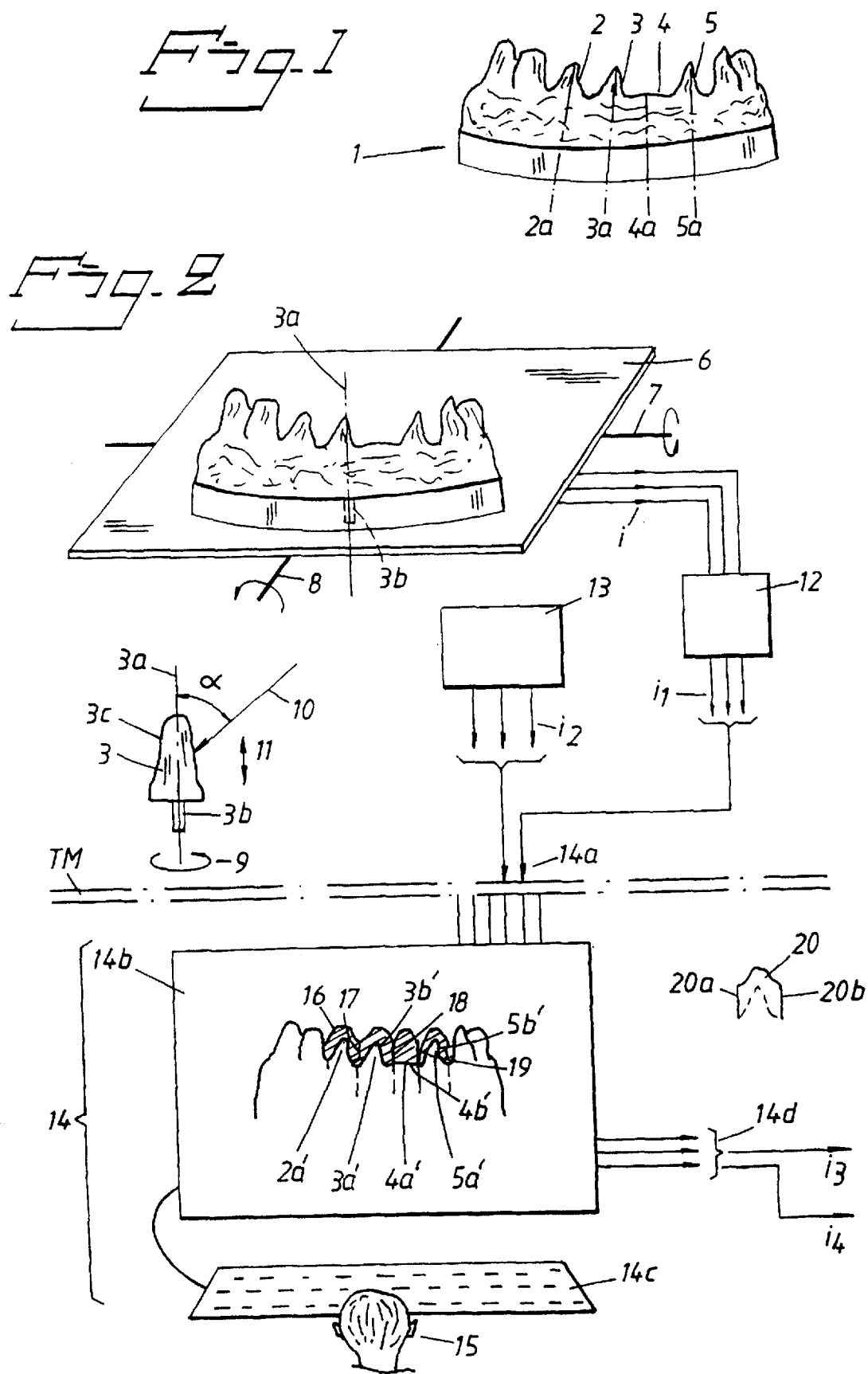

ARRANGEMENT FOR RECREATING A MODEL OF A DENTAL PRODUCT

TECHNICAL FIELD

The present invention relates to an arrangement and method for recreating all or part of a model of a dental product, or instrument for a dental product, from information implemented in or supplied to manufacturing equipment, preferably in the form of CAD equipment. In this equipment, the model/model part with associated implant and/or tooth remnant(s) in a jaw bone can be simulated, and the simulated model/model part can be completely or partially divided into the implant and/or tooth remnant parts. For recreating the model/model part, information can be extracted from the manufacturing equipment.

The invention can, for example, be applied to an arrangement or method which uses an original model of tooth remnant parts in conjunction with production systems for a dental construction, for example in the form of a dental bridge, moulds for casting, pressing, etc. In one embodiment, the arrangement can be of the type in which the system comprises a reading apparatus which reads a tooth remnant representation in the original model and works preferably in the polar coordinates system with a reading axis inclined in relation to the respective reading surface. In addition, a levelling function can also be included so that it is possible, on each reading of the tooth remnant part representation in the original model, to read all the outer surface areas of the respective representation. In addition, the system uses CAD equipment which, with the aid of position information obtained from the reading and levelling functions, is arranged to display a reproduction or simulation of all or part of the original model. In interaction with a user, it is possible, on the said reproduction or simulation, on the one hand to produce the said construction/product or to divide the construction up into construction parts and identify the contact surfaces of the construction parts in terms of position and direction according to dental rules, and, on the other hand, to produce replicas of the individual construction parts.

STATE OF THE ART

In the production of dental bridges, casting moulds and press moulds, etc., for dental constructions, it is already known to read and produce the dental construction or product in question in construction parts which are sectioned and welded together according to the system of dental rules. It is also known to scan individual tooth remnant elements in an original model of the tooth remnant constellation in question. With levelling equipment it is in this case possible to transform the individual element (the tooth remnant representation) to a centre, for example a centre of rotation, around which the scanning is based. In the CAD equipment, tooth remnant representations of the original model can be recreated in a three-dimensional environment, and in interaction with one or more users (computer equipment, databases, etc.) a construction in question, for example a dental bridge, can be created in the computer environment. Each tooth part representation can be re-transformed in the computer environment about the said centre axis (axis of rotation), in which case, in a preferred embodiment, the manufacture of the individual element can be undertaken in accordance with the reading principle, i.e. the reading system (the reading needle and bearing member for the tooth remnant element) can move in the corresponding system according to which the machining is carried out. It should be noted here that reading and machining in the polar coordinates system can afford advantages in the form of considerable accuracy of the construction produced, despite the relatively small amount of reading information, which means, inter alia, that the reading and machining times are relatively short. However, the invention provides the possibility of scanning and machining in different coordinate systems.

It is also known to bring the construction parts thus manufactured together in welding equipment and, in this equipment, to laser-weld the construction parts via established contact surfaces.

It is also known that a dentist or dental technician can order a dental product via a telecommunications and/or computer connection. The product has in this case been tested in the original model for determining the correct fit, appearance, etc., after which any readjustments have been made.

DESCRIPTION OF THE INVENTION
TECHNICAL PROBLEM

There is a need to be able to reduce the manufacturing times for different dental constructions or products or instruments for the constructions/products. It is known that dental bridges in particular can represent complex designs, which also require extremely high manufacturing precision (tolerances of about 0.01 mm). In cases where the manufacturing system and the original model are at different locations, the products or the original model have to be sent between the locations, which causes delays due to the postal service or other transport. The invention solves this problem, among others.

Hitherto, the manufacturing parts for dental bridges, especially complicated ones, have been long and have required great manual skill. It is expedient to be able to transfer or centralize areas of this skill to places and locations where there is expertise in machine handling. This paves the way for accelerated handling, while retaining high precision results. The invention is intended to solve this set of problems, among others.

The invention is based on the insight of manufacturing dental bridges by sectioning or dividing up the dental bridge construction generated in the computer equipment. There are special technical requirements that contact surfaces between construction parts must be indicated in the computer equipment and maintained through the manufacture of the construction parts and on transfer to the welding equipment. It is not already known to be able to create, for example, a whole dental bridge in a single unit. The invention also solves this problem.

In accordance with the invention, a levelling function is to be used for transforming starting positions and starting inclinations to reading and machining positions and reading and machining inclinations. It is important that an effective technical connection can be obtained between the reading, machining and levelling functions. The invention solves this problem too.

In the present invention, use is also made, in one embodiment, of the recognition that levelling panels afford the possibility of inputting information in a three-dimensional CAD environment. In this case, a position-fixing member (identification member) is used. The read-off data, the position-fixing members and information on the position of the member in the structure are sufficient for structure data to be transformed to a defined position in the three-dimensional reproduction. When all the necessary structures (representations) have been presented at their respective places in the CAD environment, construction work can begin. In accordance with the above, the said construction work can constitute the construction of a bridge on a number of prepared teeth, distancing pieces adapted to fixtures, etc. The dental constructions are, in accordance with the above, built up by forming individual parts which are then joined together to form a more complex structure, which means that the cross-sections which are later to be joined together are set out and dimensioned in accordance with current dental rules. The cross-section is given a position and a direction. The milling can take place with a centre of rotation which is identical to the centre of rotation upon reading. To achieve a very good final result, it is important that the abovementioned principles can be complied with in the novel arrangement and method associated with the invention. The invention solves this problem too.

SOLUTION

In accordance with the concept of the invention, a model will be recreated using the data of the original model input to the manufacturing equipment. That which can principally be regarded as characterizing an arrangement according to the invention is that the said information is representative of angles of inclination for two or more longitudinal axes belonging to the said implant and/or tooth remnant(s). Replicas of the said implant and/or tooth remnant parts can be individually produced by means of the manufacturing equipment. Each implant and/or tooth remnant part is designed with or comprises a position-fixing member (can also be called identification member) to make it possible to determine the individual position of rotation and inclination of the part in the recreated model/model part. Control members for one or more levelling panels and/or one or more boring machines receive the said information as control information to make it possible to form holes in a mounting member in which the holes receive angles of inclination for their longitudinal axes and positions according to the longitudinal axis inclinations and the positions for the implant and/or tooth remnant(s) of the simulated model/model part. The mounting member is arranged to receive the individually produced replicas via the holes which have been made. The replicas can be applied in the holes via their position-fixing members, and after this application the recreated model/model part has been formed.

In one embodiment, the manufacturing equipment is also arranged to permit application, on the manufacturing equipment's simulated variant, i.e. the picture displayed on a computer screen or equivalent, of the model of the product or instrument. The manufacturing equipment also permits division of the product or instrument into product or instrument parts. The said replicas can be individually produced by means of the manufacturing equipment. The last-mentioned replicas can also be applied on the replicas of the implant and/or tooth remnant parts applied on the mounting member.

The mounting member with associated replicas of implant and/or tooth remnant parts and, arranged in turn on these, replicas of product or instrument parts can be applied in jig (welding jig) in order to permit welding, by means of welding members, of the replicas of the product or instrument parts via contact surfaces which correspond to contact surfaces on the product or instrument parts in the simulated and divided variant on the computer screen of the manufacturing equipment. Control members for the said welding and/or jig members receive, as control information from the manufacturing equipment, second information which is representative of contact surfaces of the product or instrument parts, and by means of which last-mentioned control information the replicas for the product or instrument parts are welded together.

In one embodiment, the simulated model/model part can also comprise one or more whole teeth which represent divided tooth parts of the model/model parts. Replicas of the said whole tooth parts with associated position-fixing members can be manufactured by means of the manufacturing equipment. The said mounting member can be arranged, on the one hand, for formation of holes in a corresponding manner for each tooth part as for the replicas for the implant and/or tooth remnant parts, and, on the other hand, for receiving each tooth part via its position-fixing member for forming the model/model part. The mounting member is arranged to receive, in each hole formed, a member which is included in a member for fixing the angle of rotation of the replica of the implant, tooth and/or tooth remnant part in question. The member for fixing the angle of rotation can be applied from the underside of the mounting member. In one embodiment, the member for fixing the angle of rotation can be arranged with a first unit which cooperates with the material of the mounting member in order to prevent rotation of the first unit relative to the mounting unit. The member for fixing the angle of rotation can also be provided with a second unit which serves as a storage unit for the replica in question. The second unit can have stop members for fixing the angle of rotation, by means of which a corresponding member in the replica cooperates in order to prevent rotational movements relative to the storage unit and thereby to prevent rotational movement between the replica and the mounting member. The first and/or second units and the replica can have two semicircular parts which can cooperate via their straight side surfaces in order to prevent the said rotational movements between the replica and the mounting or bearing member.

A method according to the invention can principally be regarded as being characterized by the fact that angles of inclination for two or more longitudinal axes belonging to the said implant and/or tooth remnant(s) are represented by the said information. Replicas of the said implant and/ or tooth remnant parts are produced by means of the manufacturing equipment, and each implant and/or tooth remnant part is designed with a position-fixing member to make it possible to determine the individual position of rotation and inclination of the part in the recreated model/model part. The said information is received by control members for one or more levelling panels and/or one or more boring machines as control information, by means of which holes are formed in a mounting member in which the holes are given angles of inclination for their longitudinal axes and positions according to the longitudinal axis inclinations and the positions for the implant and/or tooth remnant(s) of the model/model part. The individually produced replicas of the implant and/or tooth remnant parts are applied in the holes via the said position-fixing members.

In one embodiment, a first levelling function is used for reading the respective implant and/or tooth remnant on the original model. Adjustment of the first levelling function from the respective starting position and starting inclination to the position and inclination corresponding to the reading position and the reading inclination establishes a signal transmission which is part of or forms the control of a second levelling function which effects the return from the position or inclination corresponding to the reading position and reading inclination to the said starting position and starting inclination. The signal transmission is preferably stored for reuse (control) of the second levelling function. The signal transmission is supplied to the manufacturing equipment and supply is in this context to be considered in its widest interpretation. The signal transmission can be transferred to the manufacturing location and does not itself require to be implemented in the equipment, but is simply saved.

ADVANTAGES

The invention makes available a less expensive manufacturing chain for the dental construction in question, while maintaining the high level of accuracy. The novel manufacturing principle means that the dental bridge manufacture is not completely dependent on the professional skill of the dental technician and dentist on site, but instead some of this skill can be centralized at a place with advanced mechanical support equipment. The treatment time for the patients can be substantially reduced. Conventional and well-proven equipment components can be used in the production of the dental construction. Thus, for example, known levelling panels can be used. It has been found that the manufacturing time, even for complex dental constructions, can be reduced by about 50% in relation to present-day methods and production techniques, by eliminating the need to transport models and products/instruments between different geographical locations. This increases the profits and reduces the costs to the end user. With the aid of the respective position-fixing member, respective individual elements/replicas can be oriented and placed in a defined position on a plate/base or other mounting member. With the aid of a drill, a hole is made with the correct direction and position on the plate/base so that the original model or the simulated variant of this is recreated. Thereafter, each individual part or replica of the milled bridge can be placed in the correct position. The information on where and in which direction the joining surfaces are situated is unambiguous in relation to the plate/base. By placing the plate/base in a clear and well-defined manner in the weld and thereafter indicating the position and direction of each joining surface, the weld can, in accordance with the previously known technique, identify the surfaces and join these together. A recreated model (of the original model) can be obtained at the manufacturing site and can be used as weld cushion for the product (tooth, bridge, instrument, etc.) which is to be welded together.

DESCRIPTION OF THE FIGURES

A presently proposed embodiment of an arrangement and method according to the invention will be described hereinbelow with reference to the figures, where:

FIG. 1 is a perspective view of an original model with representations for tooth remnant parts, whole teeth and a jaw bone, FIG. 2 is an outline diagram of the application of the original model on a first levelling panel, a reading function for respective tooth remnant or equivalent, signal-generating members which generate signals via a transport medium to CAD equipment with computer screen and terminal, by means of which manufacturing equipment signals are generated.

DETAILED DESCRIPTION OF FUNCTION

Figure 3:
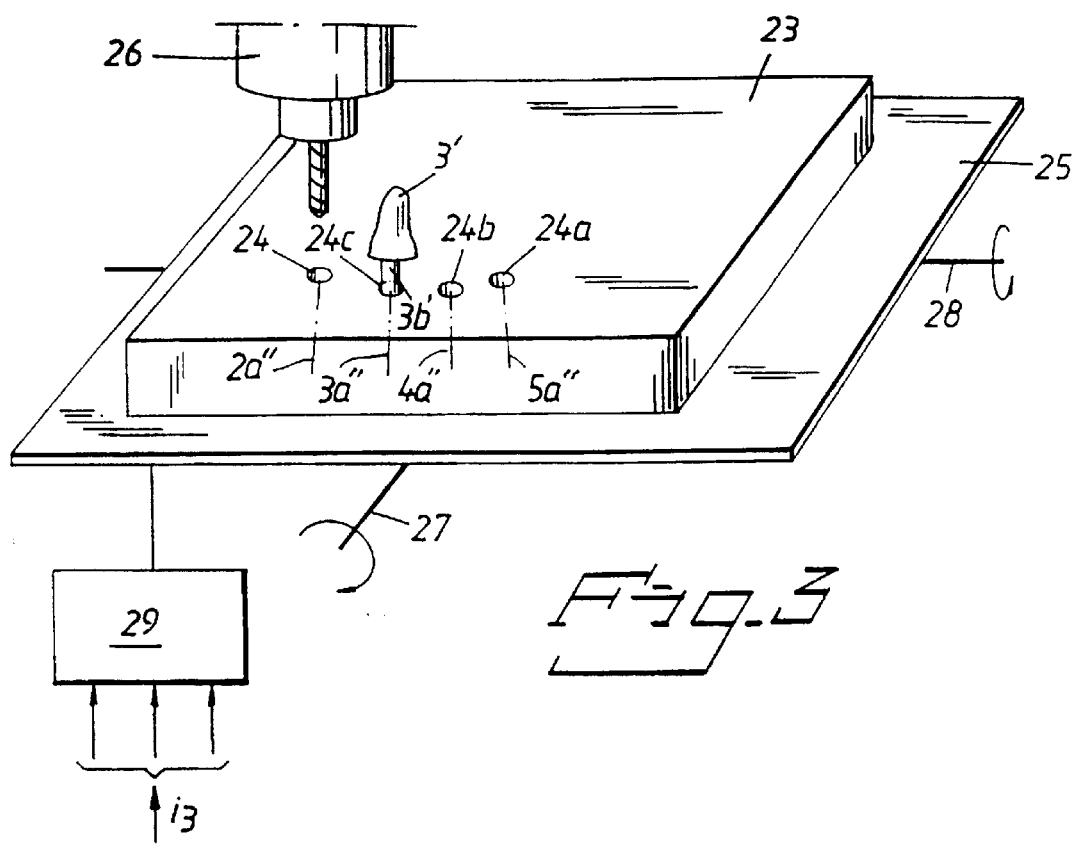
FIG. 3 is a perspective view of production equipment for the recreated model, which production equipment comprises a second levelling panel, boring equipment, and control members for the levelling panel and/or boring machine used for making holes in a mounting member applied on the levelling panel.

In FIG. 1, reference number 1 shows an original model with tooth remnant representations 2, 3, 4 and 5 from the mouth of a patient (not shown). In the present case, the representations 2–5 are located between otherwise whole teeth and are to be provided with a bridge in accordance with what is stated below. The representations have individual positions in or on the model and their longitudinal axes $2a$, $3a$, $4a$, $5a$ have individual inclinations as a function of the bite, attitude of the teeth, etc.

According to the invention, in FIG. 2 a first levelling function is used which can be obtained with a known levelling panel whose plane is shown by 6 and cardan suspension shafts by 7 and 8. With the aid of the levelling function, a tooth remnant representation, for example 3, can be defined in terms of position and inclination. The position is adjusted by means of displacing the original model on the plane (panel) 6 and the inclination is adjusted by rotating the shafts 7 and 8. The transformations in the present case mean that the longitudinal axis $3a$ of the tooth remnant representation 3 is shifted to a centre of rotation, indicated below, and assumes a vertical bearing (perpendicular bearing). The tooth remnant representation, for example at $3b$, can be built up from or consist of an implant (pin) $3b$.

The respective tooth remnant representation can be scanned in a known manner with a scanning function in which the representation is rotated about its vertical longitudinal axis $3a$, see rotation arrow 9. The scanning function (scanning needle, optic beam, etc.) is shown symbolically by 10. The scanning direction is angled towards the outer surface $3c$ by an angle $\alpha$. The scanning function 10 and the body (tooth remnant representation) 3 are longitudinally displaced in a known manner in the vertical direction in relation to one another.

Rotating the shafts 7 and 8 of the levelling function for the said adjustment of the tooth remnant part 3 to the vertical position results, in a known manner, in a signal transmission i indicating the adjustment of the plane 6 for obtaining the position and the inclination. In one embodiment, the adjustment signal is stored in a unit 12 which is given by the signals as a function of signals i1. The scanning function comprises a unit 13 which scans the reading and gives electrical (digital) information i2 on the outer contour $3c$ of the body 3. The signals i1 and i2 are thus representative of the adjustment of the levelling function, and the reading function is supplied to manufacturing equipment, preferably CAD equipment 14 of known type. The CAD equipment has an input $14a$ for receiving the said signals i1 and i2. They can be supplied via any form of transport medium TM, for example telecommunications and/or computer network, Internet, post, road transport, etc.

The CAD equipment has an image screen $14b$ (or other type of presentation means, for example sound reproduction). It also includes a terminal $14c$ by means of which one or more users 15 can cooperate interactively with the equipment in a manner known per se. With the aid of the signal transmissions i1 and i2 of the levelling function and of the reading Function, an accurate second representation or simulation of the original model is created in the CAD equipment. In the CAD equipment, by means of interaction, a dental construction, in this case a dental bridge, 16 can be built up on the representation which is created in the CAD equipment of the tooth remnant representation 2a', 3a', 4a' and 5a'. The dental bridge construction can be designed according to dental rules and in accordance with dental rules. In the FIGS., 3b', 4b' and 5b' show a part of the side surfaces of the simulated tooth remnant representations.

The dental bridge 16 is dimensioned according to dental rules, and the important aspect in this respect is the establishment of contact surfaces 17, 18 and 19 which have to be defined in terms of direction and position. With the aid of the CAD equipment 14, it is possible to produce a replica of each simulated dental bridge part 20, whose contact surfaces are indicated by 20a and 20b. Each tooth remnant representation 2, 3, 4, 5 according to FIG. 1 is read as described above. A replica 20 of the respective simulated dental bridge part is produced thereafter.

In accordance with the invention, position-fixing members will be used for obtaining the correct orientation of each replica produced, as described below.

Replicas 20 of dental bridge parts thus produced must be applied to replicas of tooth remnant representations 3'. The last-mentioned replicas are in turn. applied on or comprise holding members, reference 3b' in FIG. 3 denoting the Holding member for the replica 3' produced by means of the CAD equipment. Each holding member has the form of or comprises a part which runs in the longitudinal direction of the replica 3' and which externally can have the form of a cylinder. Each replica 3' with associated holding member 3b' is applied, according to the invention, on a mounting member or a bearing unit 23. Before the application, the bearing unit is provided with bore holes 24, whose longitudinal axes 2a", 3a", 4a", 5a" correspond in terms of position and inclination to the positions and inclinations of the original model, or of the simulated model on the screen 14, for the tooth remnant representations 2, 3, 4 and 5. By using a second levelling function 25, for example in the form of a second levelling panel, holes 24 can be formed with boring equipment 26 so that the positions 24, 24a, 24b and 24c and the inclinations of the longitudinal axes 2a", 3a", 4a" and 5a" of the holes correspond to the original model's corresponding positions and inclinations. The shafts of the second levelling panel are indicated by 27 and 28.

Figure 4:
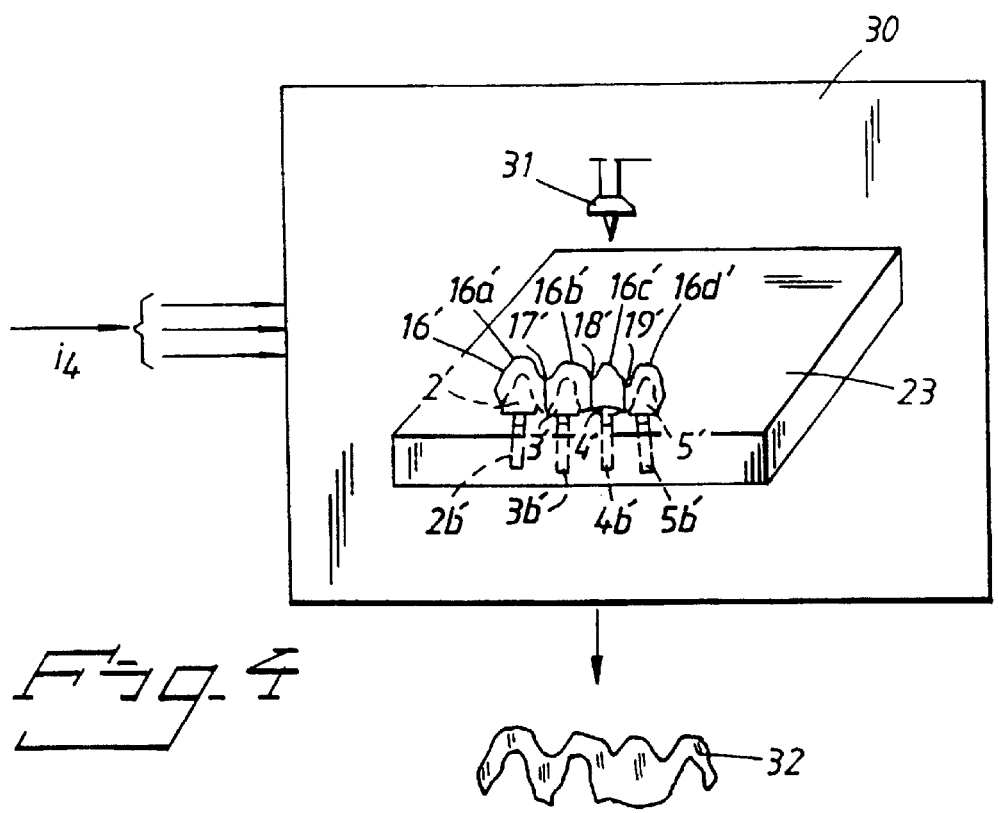
FIG. 4 shows a weld jig to which the mounting member according to FIG. 3 has been transferred with collected replicas of implant and/or tooth remnant parts and product or instrument parts, and FIG. 4 also shows a product or instrument/instrument part produced in the jig.

The second levelling panel is provided with control equipment 29 for adjusting the position of the plane 25. The boring equipment 26 is controlled in a known manner by means of the unit 29. The unit 29 is controlled from the output 14d of the CAD unit with signal/signals i4, see FIG. 2. First replicas of the implant and/or tooth remnant parts are applied on the mounting member and are arranged in the bored holes via their holding members. Thereafter, the replicas of the dental bridge parts are arranged on the first-mentioned applied replicas. The mounting member or the bearing plane 23 according to FIG. 3 is transferred according to FIG. 4 to welding equipment 30, preferably laser-welding equipment, whose laser-welding electrodes are symbolized by 31. The laser-welding equipment is supplied with information i4 from the CAD equipment, which information i4 includes information on the directions and positions of the contact surfaces 17, 18, 19. In the welding equipment, the construction parts 16a, 16b, 16c and 16d of the construction 16 are thus welded together via the said defined contact surfaces 17', 18' and 19'. The result (the product) obtained from the welding equipment, i.e. the dental bridge in question, is symbolized by 32. In FIG. 4, the holding members of the replicas 2', 3', 4' and 5' are indicated by 2b', 3b', 4b' and 5b'.

A method using an original model 1 to produce a dental construction (product, instrument, etc.) of a dental bridge, a mould for pressing or casting, etc., can, in one embodiment, be summarized as having the following stages:

a) the tooth remnant representations are read by reading equipment and levelling function, b) a reproduction or simulation of all or part of the original model is produced in CAD equipment with the aid of data from the said reading and levelling functions, c) the tooth remnants are represented in the CAD equipment and they are divided up into tooth remnant parts and are identified in equipment on longitudinal axes which run in the vertical direction of the tooth remnant parts and replicas of the tooth remnant parts are produced by means of the CAD equipment, which last-mentioned replicas comprise or are arranged with holding members and position-fixing members, d) in the CAD equipment, the said construction (product) is created, on the said simulated tooth remnant parts, the construction is divided up into construction parts, and the contact surfaces of the construction parts are identified according to dental rules, and replicas of the individual construction parts are produced by means of the CAD equipment, e) the produced replicas are mounted on a mounting member or bearing member so that they form a recreated model with applied construction, f) the replicas of the construction parts are welded together in welding equipment in which the bearing member can be installed.

The following stages can be included as subsidiary steps in accordance with the above:

g) a signal transmission is effected by means of the said levelling function, which signal transmission corresponds to the transformation of each tooth remnant representation from a starting position and a starting inclination in the original model and/or the reproduction to a reading position and reading inclination, h) a further or second levelling function (25) is controlled with the aid of a signal transmission (i4) stored in or fed to the CAD equipment in conjunction with bore holes (24) being established for holding members in the mounting member, and i) on the application of holding members, there are obtained correct inclinations on the longitudinal axes of the replicas the replicas of the simulated tooth remnant parts in the mounting member via the replicas holding members the application of holding members and correct rotational angle positions for the replicas [sic].

Figure 5:
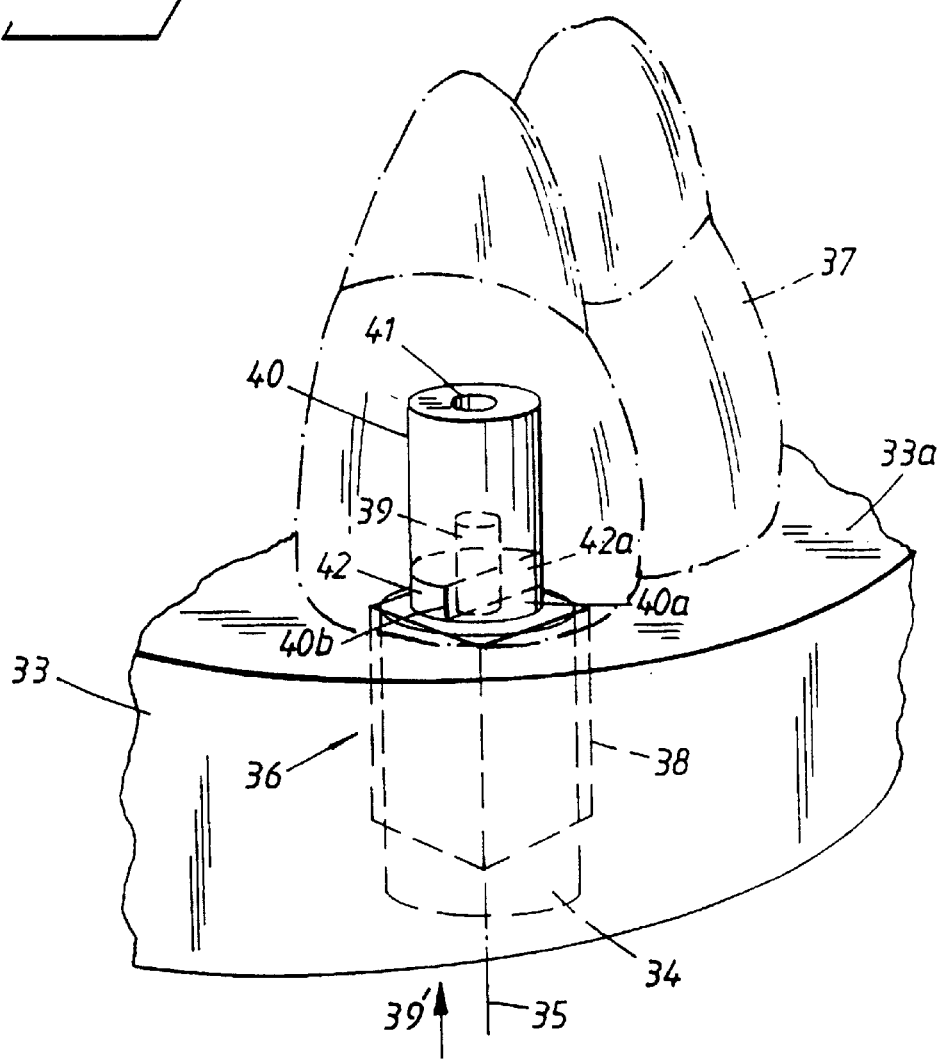
FIGS. 5, 5a show different views of an embodiment of a position-fixing member which rotationally fixes a replica relative to the mounting member.

A recreated model consisting of the replicas 2b', 3b', 4b' and 5b' can also include replicas of whole teeth, implants, etc. With the recreated model, the production of the product or the instrument 32 can be carried out at the same geographical location as the manufacture of the recreated model. In FIG. 5, the mounting member is indicated by 33 and a bore hole formed using the boring equipment (26 in FIG. 3) is indicated by 34. In addition to exact centring in the direction of the longitudinal axis, the position-fixing member (identification member) 36 must fix the direction of rotation of an actual replica 37 of a tooth remnant part relative to the mounting member 33, on which the recreated model is built up.

Figure 5A:
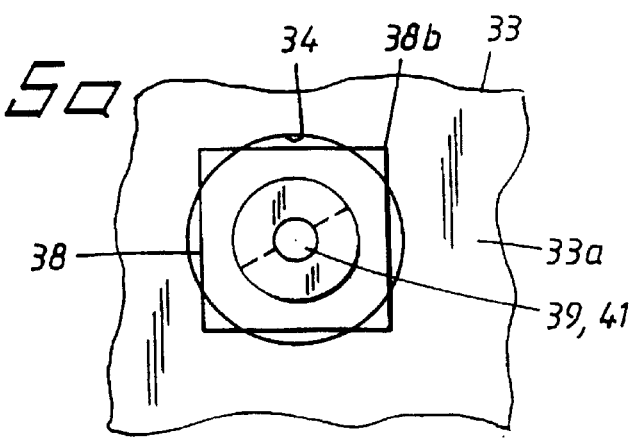

In the example according to FIG. 5, the position-fixing member comprises a first unit 38. The position-fixing member can be pressed in from the underside of the mounting member, cf. direction 39. According to FIG. 5a, the unit 38 in the embodiment shown can have a square shape (or other polygonal shape). The corners 38b extend slightly outside the cross-section of the recess 34 according to FIG. 5a. The mounting member is made of non-rigid material, for example plastic. By forcing the unit 38 into the recess, the edge 38b can dig into the material of the mounting member and in this way give the unit 38 a rotationally fixed position relative to the member 33.

The position-fixing member also has a bearing member 39 for the replica 37. The latter is made with a corresponding bearing member 40 which cooperates with the bearing member 39 in a rotationally rigid connection. In the illustrative embodiment, the member 39 consists of a cylindrical peg firmly connected to the unit 38. The second bearing member 40 has a recess 41 which can cooperate with the peg. Externally, the member 40 can have a cylindrical shape. The unit 38 has on its top a stop unit 42, for example a semicircular stop unit. At its lower end the unit 40 is designed with a corresponding semicircular part 40a which, in the position of the replica 37 on the mounting member 33 according to FIG. 5, is opposite the heel 42 so that the side surfaces 42a and 40b of the semicircular parts are opposite each other and bear against each other. The unit 40 is arranged in a fixed manner in the replica 37. The position-fixing member 38, 39, 42 is thus pressed in from underneath so that the peg 39 projects above the top surface 33a of the mounting member. The replica with the member 40, 42 is applied from above and acquires a rotationally fixed position on the mounting member and an inclined position which coincides with the longitudinal axis 35 of the bore hole.

The invention is not limited to the embodiment shown above by way of example, but can be modified within the scope of the attached patent claims and the concept of the invention.

What is claimed is:

1. An apparatus for recreating all or part of a dental product model having a number of parts, comprising:
    a means for obtaining information representative of the position and angle of inclination for the longitudinal axis of each of said number of parts within said model, said number of parts being at least one part selected from the group consisting of:
        (a) a tooth remnant replica part, and
        (b) an implant part;
    a means for simulating said number of parts within said model using said information;
    a means for individually producing said number of parts, using said information, with each said part having a corresponding position fixing member used to determine said each part's position of rotation and inclination within said model; and
    a means for boring a hole in a mounting member according to said position and angle of inclination for said longitudinal axis of said position fixing member using said information to control said boring means and a leveler supporting said mounting member,
    wherein said mounting member hole is bored to receive said position fixing member, corresponding to each said part, so that each said part's position and inclination within said model accords with said representative information.

2. The apparatus according to claim 1, wherein:
    said producing means forms each said tooth remnant replica part to receive a corresponding implant part.

3. The apparatus according to claim 2, further comprising:
    a means for welding a plurality of implant parts together, when said implant parts are arranged on said tooth remnant replica parts according to said model, at contact surfaces between said plurality of implant parts using said information to determine said contact surfaces and control said welding means.

4. The apparatus according to claim 1, further comprising:
    a mounting means for mounting each said position fixing member into said mounting member from an underside of said mounting member.

5. The apparatus according to claim 1, wherein:
    said means for obtaining information establishes a signal transmission used to control said boring means and said leveler.

6. The apparatus according to claim 1 wherein:
    said producing means forms each said position fixing member with a first unit and a second unit, said first unit having a first stop formed to cooperate with said mounting member to prevent rotation of said first unit relative to said mounting member, said second unit formed to fasten said corresponding part to said position fixing member and having a second stop to prevent rotation of said corresponding part in relation to said mounting member.

7. The apparatus according to claim 6, wherein:
    said producing means forms a semicircular end on each said first stop and said second stop and said semicircular ends of said first and second stops cooperate via the straight edges of said semicircular ends to prevent rotational movement between said mounting member and said part corresponding to said position fixing member.

8. An apparatus for recreating all or part of a dental product model having a number of parts, comprising:
    a means for obtaining information representative of the position and angle of inclination for the longitudinal axis of each of said number of parts within said model, said number of parts being at least one part selected from the group consisting of:
        (a) a tooth remnant replica part,
        (b) an implant part, and
        (c) a whole tooth replica part;
    a means for simulating said number of parts within said model using said information;
    a means for individually producing said number of parts, using said information, with each said part having a corresponding position fixing member used to determine said each part's position of rotation and inclination within said model; and
    a means for boring a hole in a mounting member according to said position and angle of inclination for said longitudinal axis of said position fixing member using said information to control said boring means and a leveler supporting said mounting member,
    wherein said mounting member hole is bored to receive said position fixing member, corresponding to each said part, so that each said part's position and inclination within said model accords with said representative information.

9. A method for recreating all or part of a dental product model having a number of parts, comprising:

obtaining information representative of the position and angle of inclination for the longitudinal axis of each of said number of parts within said model, said number of parts being at least one part selected from the group consisting of:
(a) a tooth remnant replica part, and
(b) an implant part;

simulating said number of parts within said model using said information;

producing said number of parts, using said information, with each said part having a corresponding position fixing member used to determine each said part's position of rotation and inclination within said model;

boring a hole in a mounting member according to said position and angle of inclination for said longitudinal axis of said position fixing member using said information to control said boring means and a leveler supporting said mounting member; and mounting said position fixing member corresponding to each said part so that each said part's position and inclination within said model accords with said representative information.

* * * * *